United States Patent [19]
Hardten

[11] Patent Number: 5,928,140
[45] Date of Patent: Jul. 27, 1999

[54] ILLUMINATED IRIS RETRACTOR PROBE SYSTEM

[76] Inventor: David R. Hardten, 2515 Kelly Ave., Excelsior, Minn. 55331

[21] Appl. No.: 08/920,128

[22] Filed: Sep. 2, 1997

[51] Int. Cl.⁶ ................................................ A61B 17/02
[52] U.S. Cl. ........................ 600/236; 600/127; 600/217
[58] Field of Search .................................. 600/236, 245, 600/210, 212, 217, 235, 127, 171, 197, 198, 199; 606/16, 17

[56] References Cited

U.S. PATENT DOCUMENTS

| | | | |
|---|---|---|---|
| 1,706,500 | 8/1929 | Smith | 600/245 |
| 2,235,979 | 3/1941 | Brown . | |
| 3,592,199 | 7/1971 | Ostensen . | |
| 3,641,332 | 2/1972 | Reick et al. | 600/245 |
| 4,579,116 | 4/1986 | Catalano | 600/236 |
| 4,870,952 | 10/1989 | Martinez . | |
| 4,878,487 | 11/1989 | Sinnett . | |
| 5,054,906 | 10/1991 | Lyons, Jr. | 600/236 |
| 5,078,712 | 1/1992 | Easley et al. . | |
| 5,156,604 | 10/1992 | Hessel et al. | 600/245 |
| 5,351,168 | 9/1994 | Easley . | |
| 5,545,153 | 8/1996 | Grinblat et al. . | |
| 5,716,328 | 2/1998 | Grieshaber et al. | 600/236 |

*Primary Examiner*—John P. Leubecker
*Assistant Examiner*—Ira Hatton
*Attorney, Agent, or Firm*—Hugh D. Jaeger

[57] ABSTRACT

The illuminated iris retractor probe system is a medical device for use in ophthalmic surgery, particularly anterior segment and posterior segment surgery where visualization of ocular structures is required. The device utilizes a handpiece to support a 23-gauge sheathed fiber optic element that transmits the illumination. The 23-gauge dimension of the sheathed fiber optic element allows it to be inserted through self-sealing incisions of 1.5–2.0 mm in size in the peripheral cornea, thereby allowing the incision to be self-sealing and thus avoiding the operative intervention and postoperative complications of sutures. The tip of the illuminated iris retractor probe has a backward bend or hook whose peripheral end is flush with the illumination end of a fiber optic element which is surrounded by a metal sheath. The specific angle of the hook and its location allows the probe to retract the iris during anterior segment procedures. This allows illumination of the peripheral vitreous to permit a more thorough vitrectomy in the anterior segment. The tip is designed to permit retraction of the iris without damaging the iris. The fiber optic element is attached to a light source connector which allows a tight connection to a halogen fiber optic light source.

19 Claims, 5 Drawing Sheets

ILLUMINATED IRIS RETRACTOR PROBE SYSTEM

CROSS REFERENCES TO CO-PENDING APPLICATIONS

None.

BACKGROUND OF THE INVENTION

1. Field of the Invention

The present invention is for an ophthalmic surgical instrument, and more particularly, pertains to an illuminated iris retractor probe system. The illuminated iris retractor probe is intended for use in ophthalmic surgery for both the anterior and posterior segments. The small diameter 23-gauge size allows for insertion through a clear corneal incision as well as through pars plana vitrectomy sites. The most typical use is for indirect illumination of the anterior vitreous, yet it also provides adequate illumination for posterior vitreous work. Small pupil cases are especially augmented with this device because of the ability to retract the iris. Other anterior segment procedures which are more adequately visualized with indirect lighting are also augmented by this device. Patients with dense cataracts where there is limited red reflex and the pupil is small benefit by the illuminated iris retractor probe. The pupil can be drawn peripherally, and the anterior capsule can then be torn visualizing it with indirect illumination. Proper illumination typically requires placing the microscope light on very dimly and using full illumination from the illuminated iris retractor probe at various oblique angles to maximize the view.

2. Description of the Prior Art

Older methods of removing vitreous from the anterior chamber included utilizing a light probe without an iris manipulator. Often in this situation, vitreous is left behind the iris in the areas of the incisions because of inadequate visualization, especially in cases where the pupil is quite small. The ability to retract the iris allows full visualization of the vitreous. Vitreous then can be removed by the ciliary processes.

Previous methods to try to manipulate tissues have been limited in their utility because of interference with a light beam at the end of the probe or additional size of the light probe which prevents insertion through a sutureless incision.

Larger light probes have the disadvantage of requiring sutures to seal the incisions necessary to place them in the eye. Sutures can cause corneal astigmatism and could potentially cause neovascularization of the peripheral cornea.

In other light probes that have been utilized in the past, the diameter is typically of 20 gauge for use in the eye, and the retracting devices at the end of the tip utilize a forward bend to manipulate retinal tissues.

One of the unique aspects of the illuminated iris retractor probe of the present invention is its specific design to allow retraction of the iris while still maintaining the placement of the probe in the anterior segment and serving as an illuminator.

SUMMARY OF THE INVENTION

During ophthalmic surgery, visualization of the various structures of the eye is quite important. The vitreous tissue is nearly clear and, therefore, direct illumination typically does not show the vitreous. Indirect illumination is very helpful. Most surgeons in the past have avoided indirect illumination when working the anterior segment because of the large size of the light probes needed to work in the anterior segment. This has required two or more incisions into the cornea that typically need sutures, which can cause astigmatism. The smaller diameter of this illuminated iris retractor probe solves this problem by allowing a self-sealing incision. The most difficult cases are those where the pupil is extremely small, thus decreasing the illumination into the posterior segment as well as decreasing access to the tissue. A backward bend on the light probe allows retraction of the iris and illumination all with one instrument, thereby allowing the other hand to remove and manipulate the vitreous.

It is important to allow illumination and retraction in one device because the surgeon is typically utilizing the other hand to perform the vitrectomy or other tissue manipulation. The 23-gauge size of the illuminated iris retractor probe is ideal because it is large enough to allow adequate illumination for removal of anterior and posterior vitreous, yet is small enough to insert through a self-sealing corneal incision.

According to one embodiment of the present invention, the illuminated iris retractor probe is composed of a handpiece with a fiber optic element within the handpiece. There is a fiber optic member or cord which secures to a connector which, in turn, connects to a fiber optic light source. The reversed hook tip of the instrument is unique in that there is a metal backward bend, which forms a reversed hook tip, that begins flush with the tip of the light probe. The reversed hook tip of the illuminated iris retractor probe has a formed bend or hook that is optimal for iris retraction.

The illuminated iris retractor probe includes a metal sheath which shields the fiber optic light. The tip of the illuminated iris retractor probe has a backward bend that allows manipulation of the iris while still allowing adequate visualization. The bend for the tip of the probe starts immediately at the illumination end of the fiber optic element and bends backward in a plane parallel to the fiber optic element.

The illuminated iris retractor probe, for manipulating the iris and visualizing vitreous for removal, includes a handpiece made of non-reflecting black plastic. The illuminated iris retractor probe handpiece has annular rings which form corrugated edges to allow a firm grip even while wearing gloves. There is a wide annular recess for the fingers to assist in manipulation. The fiber optic member or cord is of 23-gauge size and is of adequate length to reach to the fiber optic light source. Various adapters are available to allow it to adapt to any commercially available light source.

One significant aspect and feature of the present invention is an illuminated iris retractor probe having a reversed hook tip and a fiber optic illumination element.

Another significant aspect and feature of the present invention is a substantially one-piece illuminated iris retractor probe providing for retraction of the iris and the illumination of areas about and adjacent to the iris.

Yet another significant aspect and feature of the present invention is the ability of the illuminated iris retractor probe to manipulate the iris, have a small diameter, and still allow adequate illumination of the anterior segment vitreous.

Still another significant aspect and feature of the present invention is an illuminated iris retractor probe which is small and, therefore, will pass through a small incision, thereby eliminating the need for sutures.

An additional significant aspect and feature of the present invention is an illuminated iris retractor probe which provides for optimal retraction of the iris.

A further significant aspect and feature of the present invention is that the illuminated iris retractor probe is gas sterilizable so that it can be utilized in surgical procedures.

A still further significant aspect and feature of the present invention is that the illuminated iris retractor probe is designed to be utilized in a single use fashion but is capable of gas sterilization.

Having thus described embodiments of the present invention, it is the principal object of the present invention to provide an illuminated iris retractor probe system.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
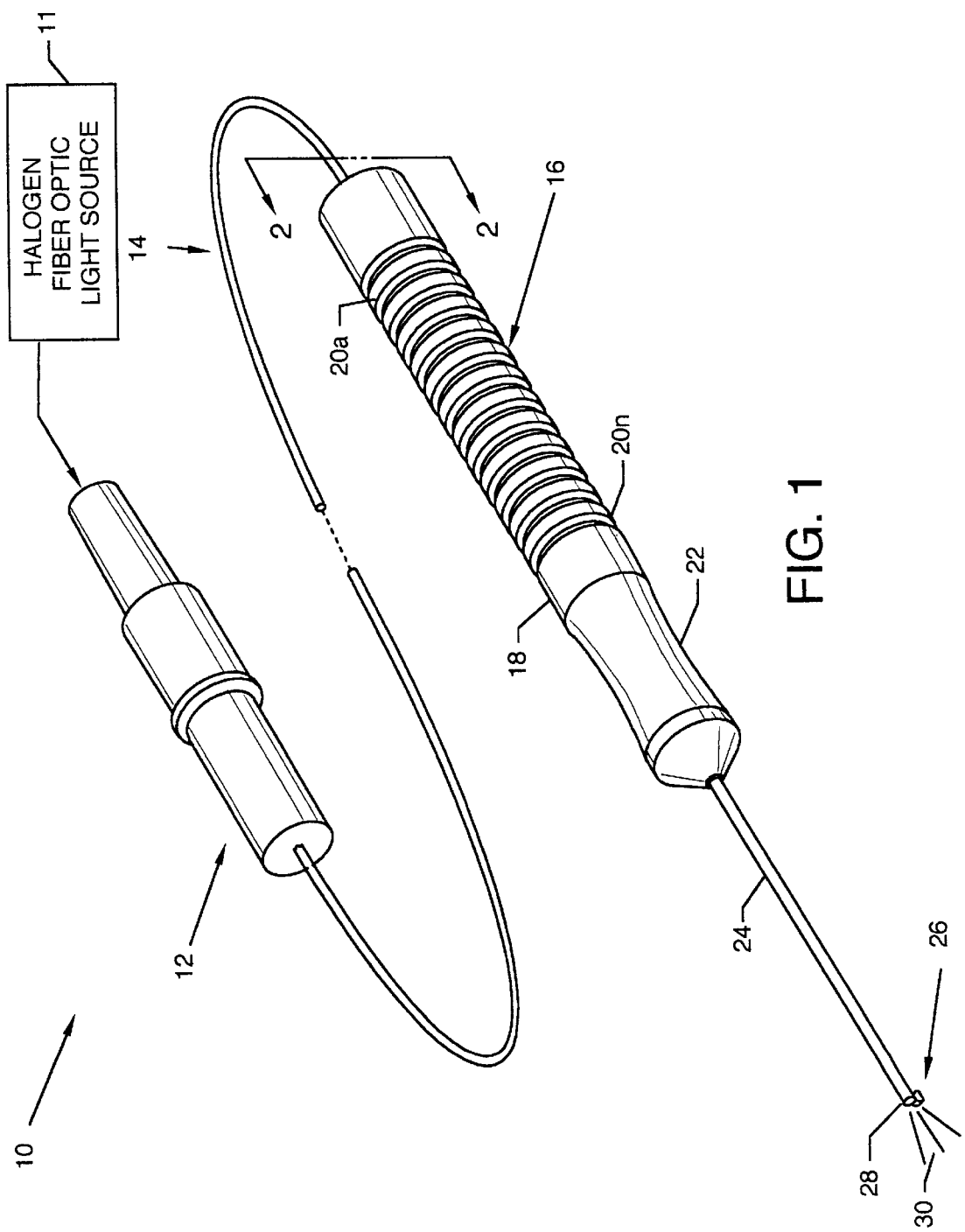
FIG. 1 illustrates an isometric view of the illuminated iris retractor probe system, the present invention.

FIG. 1 illustrates an isometric view of an illuminated iris retractor probe system 10, the present invention, including a halogen fiber optic light source 11, a configured light source connector 12, a flexible fiber optic member or cord 14 and an illuminated iris retractor probe 16 which is manually manipulated with one hand during eye surgery. The illuminated iris retractor probe 16 includes a configured probe handpiece 18 which is preferably fabricated of non-reflecting black plastic, but which can be formed of rubber, metal or other suitable material, having a plurality of annular rings 20a–20n along a major portion of its length and a wide annular recess 22 along a minor portion of its length, each for aiding in grasping of the illuminated iris retractor probe 16 during surgical procedures, even while wearing gloves. Extending from the distal end of the configured probe handpiece 18 is a sheath 24, preferably of metal such as stainless steel, but which can be formed of other suitable material. A reverse hook tip 26, being integral to the sheath 24, is located at the distal end 28 of the sheath 24. Located interior to the sheath 24 and extending to the distal end 28 of the sheath 24 is the distal end of a fiber optic element constituting the center portion of the fiber optic member 14, as illustrated and described in detail in FIGS. 2 and 3. Light 30 is transmitted by the center and distal portion of the fiber optic member 14 located at the area adjacent to the distal sheath end 28 and reverse hook tip 26 for illumination of the vitreous, or other areas, during a vitrectomy or other surgical technique. The reverse hook tip 26 of the sheath 24 is available for manipulation and/or retraction of the iris, as later described in detail.

Figure 2:
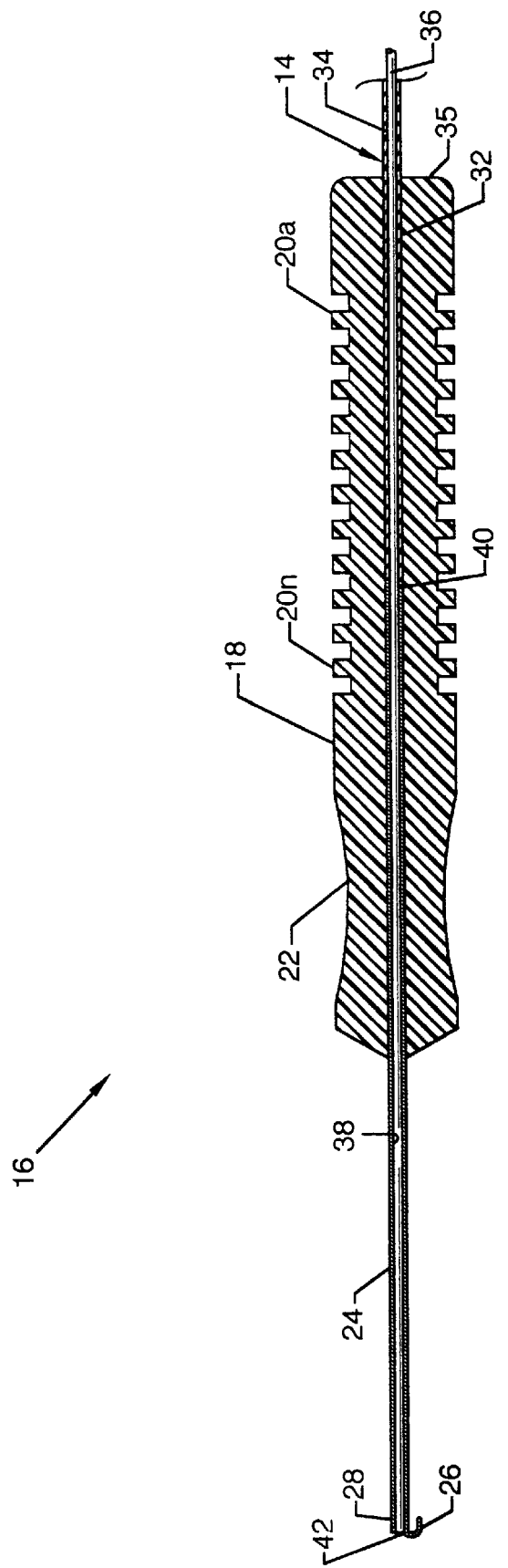
FIG. 2 illustrates a cross sectional view of the illuminated iris retractor probe along line 2—2 of FIG. 1.

FIG. 2 illustrates a cross sectional view of the illuminated iris retractor probe 16 along line 2—2 of FIG. 1, where all numerals correspond to those elements previously described. A central longitudinal bore 32 aligns along the center of the configured probe handpiece 18 to accommodate the fiber optic member 14 and the sheath 24. The fiber optic member 14 includes an outer opaque covering 34 and a centrally located fiber optic element 36. The fiber optic member 14, including the outer opaque covering 34 and the centrally located fiber optic element 36, aligns in the central longitudinal bore 32 and extends distally from the proximal end 35 of the configured probe handpiece 18. The outer opaque covering 34 extends to the mid-portion of the central longitudinal bore 32 to meet and align with the proximal end 40 of the sheath 24. The centrally located fiber optic element 36 continues past the junction of the opaque covering 34 and proximal end 40 of the sheath 24 and continues in alignment within the central bore 38 of the sheath 24 to the distal end 28 of the sheath 24. The distal end 42 of the fiber optic element 36 is heat molded and/or polished to stabilize the distal end 42 of the fiber optic element 36 and to enhance the light emitting properties of the fiber optic element 36 as well as sealing the distal end 42 of the fiber optic element 36. The distal end 42 of the fiber optic is at the distal end 28 of the sheath, although the placement can be slightly forward or rearward of the distal end of the sheath. The reverse hook tip 26 is integral to and is formed of the same material used for the sheath 24.

Figure 3:
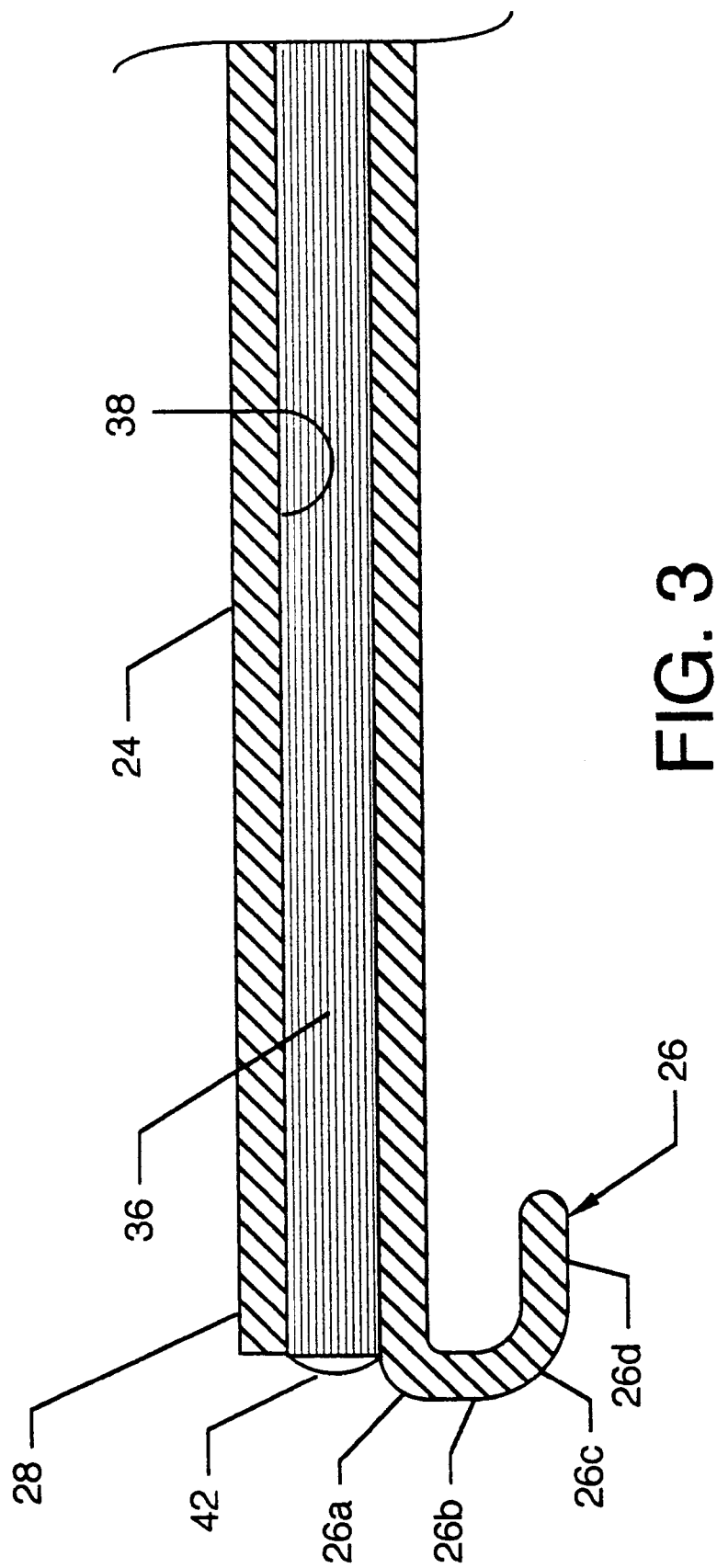
FIG. 3 illustrates a side view of the reverse hook tip.

FIG. 3 illustrates a side view of the reverse hook tip 26, where all numerals correspond to those elements previously described. The reverse hook tip 26 includes a curved portion 26a extending from the sheath 24, a generally planar substantially vertical portion 26b extending downwardly from the curved portion 26a, a curved portion 26c extending from the generally planar substantially vertical portion 26b, and a substantially horizontal portion 26d extending from the curved portion 26c substantially parallel to the sheath 24 in the proximal direction. Although the reverse hook tip is shown as extending substantially horizontally and portion 26d substantially parallel to the sheath 24, the portion 26d could extend at an oblique angle, if desired, and such is not deemed to be limiting as to the scope of the invention. In the alternative, the reverse hook tip 26 could even assume a "c" or other such configured shape that can be utilized according to the teachings of the invention.

Figure 4:
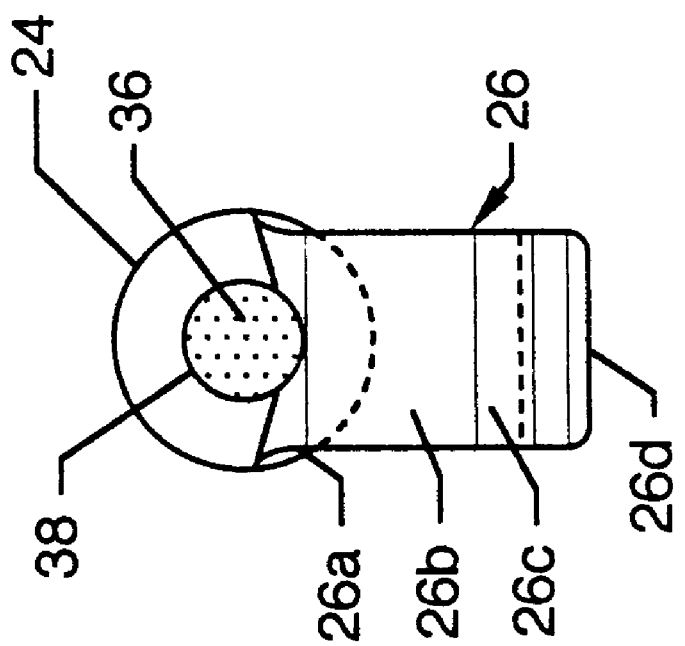
FIG. 4 illustrates an end view of the reverse hook tip.

FIG. 4 illustrates an end view of the reverse hook tip 26, where all numerals correspond to those elements previously described.

MODE OF OPERATION

Figure 5:
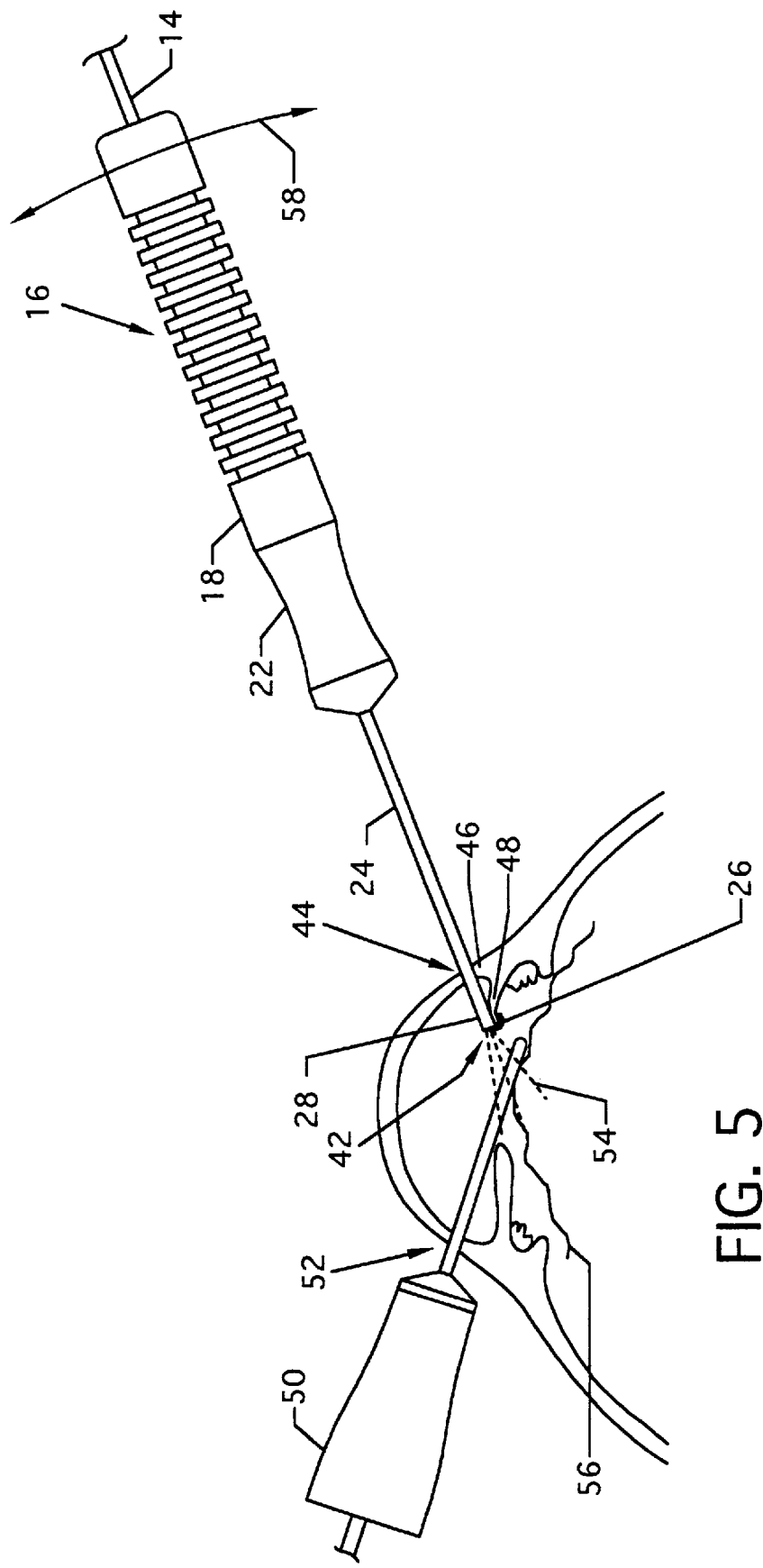
FIG. 5 illustrates the illuminated iris retractor probe in use in a vitrectomy.

FIG. 5 best illustrates the mode of operation of the illuminated iris retractor probe 16 in use in a vitrectomy, where all numerals correspond to those elements previously described. The distal end 28 is inserted in a small incision 44 in the peripheral cornea 46 and is maneuvered to position the reverse hook tip 26 into intimate capturing contact with the annular edge of the iris 48. The illuminated iris retractor probe 16 is then manipulated to position the iris 48 to allow for introduction of the distal end of a vitrector 50, or other suitable surgical device, through an additional small incision 52 in the peripheral cornea 46 and into the area behind the iris containing the vitreous. Illumination 54 from the distal fiber optic element end 42 indirectly illuminates the vitreous 56 for subsequent removal thereof by the vitrector 50. The configured probe handpiece 18, which is held and positioned by one hand, can be maneuvered, as indicated by maneuver arrow 58, substantially about and/or through the incision 44 to illuminate various vitreous areas while still maintaining effective control over the repositioned annular edge of the iris 48.

The illuminated iris retractor probe is currently being utilized for ophthalmic surgery of the anterior and posterior segments that requires both illumination and manipulation of tissues. Procedures that it has been used for to date include cataract extraction, subtotal vitrectors with placement of a secondary intraocular lens, and penetrating keratoplasty. During cataract extraction, this device is useful to indirectly illuminate anterior segment structures. Especially useful is the illumination of the anterior capsule during capsulotomy or capsulorhexis. During this use, the light probe can be placed through a standard paracentesis site of 1.5–2.0 mm and be utilized to illuminate the anterior capsule when the red reflex is poor. This can allow adequate visualization of the capsule to perform a round capsulorhexis, whereas with typical microscope lighting, the anterior capsule cannot be visualized when the red reflex is poor, as in cases with an extremely dense nucleus or in the presence of vitreous hemorrhage. The fact that the light probe has a 23-gauge construction allows it to be passed through a 1.5–2.0 mm clear corneal incision. This size incision will not require suturing for closure, therefore avoiding the complication of such sutures. The special design of the iris retractor allows the iris to be drawn peripherally to further expose the anterior segment structures, including the anterior capsule in this specific use. Illumination is able to be maintained continuously because the light probe can stay within the eye, even with maximal iris retraction.

Other uses of the illuminated iris retractor probe include anterior vitrectomy. This procedure would be common in the cases of secondary intraocular lens implantation where vitreous has prolapsed into the anterior chamber, or cases of cataract extraction with a torn posterior capsule and vitreous prolapse. The microscope light can then be turned off and the light probe used to adequately visualize the vitreous in an indirect fashion. This allows visualization of the difficult-to-see vitreous. The iris hook can then be used to retract the iris, which is especially useful in small pupil cases. Thorough clearing of the vitreous from the anterior segment is important in reducing cystoid macular edema.

At the time of penetrating keratoplasty through an open sky approach, the light probe is also useful for adequately visualizing the vitreous and associated structures. It can also be used to visualize the iris and anterior segment structures while placing a transsclerally sutured posterior chamber lens.

Various modifications can be made to the present invention without departing from the apparent scope hereof.

I claim:

1. A probe element for use in eye surgery, comprising: an elongated tubular metallic sheath having a longitudinal axis, said elongated tubular metallic sheath having a reversely bent hook tip formed integrally in one piece therewith at one end thereof, said reversely bent hook tip beginning flush with said one end of said tubular metallic sheath and having a first portion extending outwardly in a direction away from said longitudinal axis of said tubular metallic sheath and a second portion unitary with said first portion and extending from said first portion toward the other end of said tubular metallic sheath.

2. The probe element as defined in claim 1, and wherein the dimension of the outside diameter of said tubular metallic sheath is 23 gauge.

3. The probe element as defined in claim 1, and wherein said tubular metallic sheath and said integrally formed reversely bent hook tip are made of stainless steel.

4. The probe element as defined in claim 1, and wherein said second portion of said reversely bent hook tip lies parallel to said longitudinal axis of said tubular metallic sheath.

5. The probe element as defined in claim 1, and wherein said second portion of said reversely bent hook tip extends obliquely with respect to said longitudinal axis of said tubular metallic sheath.

6. An iris retractor probe, comprising:
   a. an elongated handpiece having a proximal end, a distal end, and a longitudinal bore extending entirely therethrough from said proximal end to said distal end;
   b. a tubular metallic sheath having a longitudinal axis, a proximal end and a distal end, said proximal end of said tubular metallic sheath being located and anchored within said longitudinal bore of said elongated handpiece, and said distal end of said tubular metallic sheath protruding outwardly from said longitudinal bore of said elongated handpiece beyond said distal end of said elongated handpiece;
   c. a reversely bent hook tip formed integrally in one piece with said tubular metallic sheath at said distal end of said tubular metallic sheath, said reversely bent hook tip beginning immediately at said distal end of said tubular metallic sheath and having a first portion extending in a direction away from said longitudinal axis of said tubular metallic sheath and a second portion unitary with said first portion and extending from said first portion rearwardly toward said proximal end of said tubular metallic sheath; and,
   d. a fiber optic element entering said longitudinal bore of said elongated handpiece at said proximal end of said elongated handpiece, extending along said longitudinal bore and into said tubular metallic sheath, and having a distal end terminating adjacent to said distal end of said tubular metallic sheath.

7. The iris retractor probe as defined in claim 6, and wherein the dimension of the outside diameter of said tubular metallic sheath is 23 gauge.

8. The iris retractor probe as defined in claim 6, and wherein said tubular metallic sheath and said integrally formed reversely bent hook tip are made of stainless steel.

9. The iris retractor probe as defined in claim 6, and wherein said elongated handpiece is made of non-reflecting black plastic.

10. The iris retractor probe as defined in claim 6, and wherein said elongated handpiece has an outer surface which includes a plurality of annular rings for aiding in grasping said elongated handpiece.

11. The iris retractor probe as defined in claim 6, and wherein said fiber optic element is permanently anchored to said elongated handpiece such that said distal end of said fiber optic element is at a fixed position with respect to said distal end of said tubular metallic sheath.

12. The iris retractor probe as defined in claim 6, and wherein said second portion of said reversely bent hook tip lies parallel to said longitudinal axis of said tubular metallic sheath.

13. The iris retractor probe as defined in claim 6, and wherein said second portion of said reversely bent hook tip extends obliquely with respect to said longitudinal axis of said tubular metallic sheath.

14. An illuminated iris retractor probe system for use in eye surgery, comprising:
   a. an elongated handpiece having a proximal end, a distal end, and a longitudinal bore extending entirely therethrough from said proximal end to said distal end;
   b. a tubular metallic sheath having a longitudinal axis, a proximal end and a distal end, said proximal end of said tubular metallic sheath being located and anchored within said longitudinal bore of said elongated handpiece, and said distal end of said tubular metallic sheath protruding outwardly from said longitudinal bore of said elongated handpiece beyond said distal end of said elongated handpiece;

c. a reversely bent hook tip formed integrally in one piece with said tubular metallic sheath at said distal end of said tubular metallic sheath, said reversely bent hook tip beginning immediately at said distal end of said tubular metallic sheath and having a first portion extending in a direction away from said longitudinal axis of said tubular metallic sheath and a second portion unitary with said first portion and extending from said first portion rearwardly toward said proximal end of said tubular metallic sheath;

d. a light source; and, e. a fiber optic element entering said longitudinal bore of said elongated handpiece at said proximal end of said elongated handpiece, extending along said longitudinal bore and into said tubular metallic sheath, having a distal end terminating adjacent to said distal end of said tubular metallic sheath, and having a proximal end connected to said light source; whereby, in use, said reversely bent hook tip is indirectly illuminated by light passing through said fiber optic element from said light source to said distal end of said fiber optic element.

15. The illuminated iris retractor probe system as defined in claim 14, and wherein said light source is a halogen light source.

16. The illuminated iris retractor probe system as defined in claim 14, and wherein the dimension of the outside diameter of said tubular metallic sheath is 23 gauge.

17. The illuminated iris retractor probe system as defined in claim 14, and wherein said tubular metallic sheath and said integrally formed reversely bent hook tip are made of stainless steel, and wherein said elongated handpiece is made of non-reflecting black plastic.

18. The illuminated iris retractor probe system as defined in claim 14, and wherein said second portion of said reversely bent hook tip lies parallel to said longitudinal axis of said tubular metallic sheath.

19. The illuminated iris retractor probe system as defined in claim 14, and wherein said fiber optic element includes an outer opaque covering which extends from said proximal end of said fiber optic element connected to said light source up to said proximal end of said tubular metallic sheath.

* * * * *